United States Patent
Nandi et al.

(10) Patent No.: US 10,253,005 B2
(45) Date of Patent: Apr. 9, 2019

(54) PROCESS FOR THE PREPARATION OF MIRABEGRON ALPHA-FORM CRYSTALS

(71) Applicants: AUROBINDO PHARMA LTD, Hitech, Hyderabad, Telangana (IN); Sukumar Nandi, Hyderabad (IN); Shantan Kumar Reddy, Hyderabad (IN); Gona Bala Narashimha Reddy, Hyderabad (IN)

(72) Inventors: Sukumar Nandi, Hyderabad (IN); Shantan Kumar Reddy, Hyderabad (IN); Gona Bala Narashimha Reddy, Hyderabad (IN); Sivakumaran Meenakshisundaram, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 0 days.

(21) Appl. No.: 15/741,859

(22) PCT Filed: May 9, 2016

(86) PCT No.: PCT/IB2016/052631
§ 371 (c)(1),
(2) Date: Jan. 4, 2018

(87) PCT Pub. No.: WO2016/181283
PCT Pub. Date: Nov. 17, 2016

(65) Prior Publication Data
US 2018/0194743 A1  Jul. 12, 2018

(30) Foreign Application Priority Data
May 11, 2015 (IN) .......................... 2389/CHE/2015

(51) Int. Cl.
*C07D 277/40* (2006.01)
(52) U.S. Cl.
CPC .................. *C07D 277/40* (2013.01)
(58) Field of Classification Search
CPC ..................................... C07D 277/40
See application file for complete search history.

(56) References Cited

U.S. PATENT DOCUMENTS

2014/0206729 A1* 7/2014 Peddy .................. C07D 277/40
514/370

* cited by examiner

*Primary Examiner* — Shawquia Jackson
(74) *Attorney, Agent, or Firm* — Jay R Akhave

(57) ABSTRACT

The present invention provides a process for the preparation of α-Form crystals of Mirabegron using a solvent selected from water.

5 Claims, 2 Drawing Sheets

PROCESS FOR THE PREPARATION OF MIRABEGRON ALPHA-FORM CRYSTALS

FIELD OF THE INVENTION

The present invention relates to a process for the preparation of Mirabegron α-Form crystals of Formula (I).

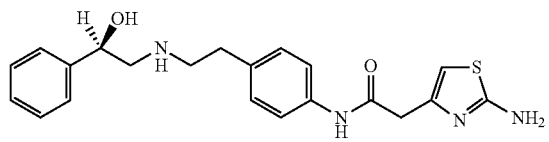

Formula I

BACKGROUND OF THE INVENTION

Mirabegron is chemically known as 2-(2-aminothiazol-4-yl)-N-[4-(2-{[(2R)-2-hydroxy-2-phenylethyl]amino}ethyl)phenyl]acetamide (I).

Mirabegron is a beta-3 adrenergic agonist indicated for the treatment of overactive bladder (OAB) with symptoms of urge urinary incontinence, urgency, and urinary frequency. Mirabegron is marketed under the trade name Myrbetriq®.

U.S. Pat. No. 6,346,532 discloses Mirabegron or its salt thereof and process for its preparation.

U.S. Pat. No. 7,342,117 discloses polymorphic forms of Mirabegron namely α-Form crystals and β-Form crystals of Mirabegron.

According to the US '117 patent, α-Form crystals of Mirabegron (characterized by an X-ray powder diffraction pattern having peaks expressed as 2θ at about 5.32, 8.08, 15.28, 17.88, 19.04, 20.20, 23.16 and 24.34 degrees and further characterized by differential scanning calorimetry exhibiting a single endotherm with a peak temperature of about 142 to 146° C.) can be prepared by adding of β-Form crystals of Mirabegron with water and alcohol and heating at about 80° C. and cooling the solution. The resulting solution was seeded to provide the α-Form crystals of Mirabegron.

According to the US '117 patent, β-Form crystals of Mirabegron (characterized by an X-ray powder diffraction pattern having peaks expressed as 2θ at about 9.68, 19.76, 20.72, 22.10 and 23.52 degrees and further characterized by differential scanning calorimetry exhibiting two broad endotherms with peak temperature of about 90° C. to 110° C. and 142 to 146° C.) can be prepared by reacting aminophenyl aminophenethanol hydrochloride (II) with 2-amino-4-thiazoleacetic acid (III) in the presence of 1-(3-dimethylaminopropyl)-3-ethylcarbodiimide monohydrochloride (EDC) and further treated with sodium hydroxide in DM water to produce wet cake of β-Form crystal of Mirabegron. This wet β-Form crystal of Mirabegron is treated with water and alcohol and the resulting solution was cooled and filtered to dryness.

The process is as shown in Scheme-I below:

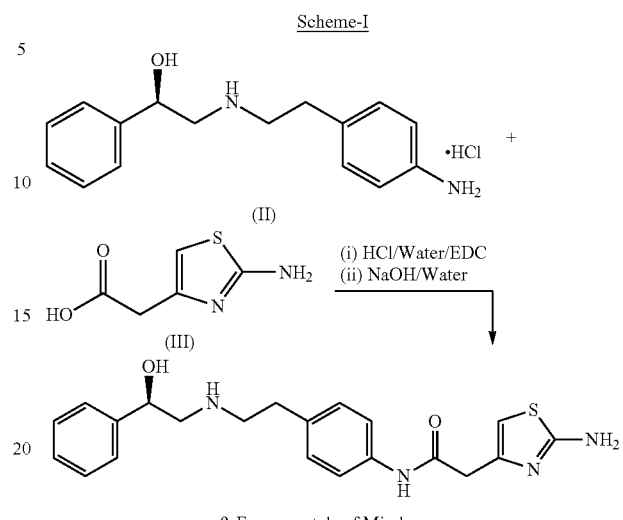

β-Form crystals of Mirabegron

US 2014/0206729 A1 discloses a process for the preparation of α-Form crystals of Mirabegron by dissolving Mirabegron in a solvent selected from methanol, ethanol, tetrahydrofuran, ethyl acetate, toluene or mixtures thereof to provide a solution, cooled the solution and isolated Mirabegron α-Form crystals.

US '729 also discloses variant process for the preparation of α-Form crystals of Mirabegron by dissolving Mirabegron in a mixture of methanol and water to provide a solution, cooled the solution and isolated α-Form crystal of Mirabegron.

US '729 also discloses variant process for the preparation of α-Form crystals of Mirabegron by providing a solution of Mirabegron in a solvent selected from tetrahydrofuran, methanol, ethanol, acetone, acetonitrile, 1,4-dioxane, methyl isobutyl ketone, chlorobenzene or mixtures thereof; combining the solution with an anti-solvent selected from cyclohexane, methylcyclohexane, n-heptane, diisopropyl ether, methyl tertiary butyl ether, toluene, water, provided that when methanol was used as a solvent then anti-solvent was other than water; and isolated α-Form crystal of Mirabegron.

WO 2015/044965 A1 discloses a process for the preparation of α-Form crystals of Mirabegron by adding first solvent to the reaction mass of Mirabegron and then basifying the solution and optionally heated the reaction mixture. Separated the organic layer and washed with water and separated organic layer followed by adding second solvent to obtain α-Form crystals of Mirabegron.

α-Form crystals of Mirabegron prepared by above prior art process contain polymeric impurities or by-products originating from production processes or storage, which gives α-Form crystals of Mirabegron with low purity and assay. Pure α-Form crystals of Mirabegron preparation involves repeated crystallization and loss of yield.

The present invention is directed to a new, efficient and eco friendly process for the preparation of α-Form crystals of Mirabegron in pure form without any organic solvent. The present inventors attempted various crystallization methods without using any organic solvents at several temperatures with a certain amount of Mirabegron.

The present inventors worked on crystallization techniques and found that dilution, and temperature plays an important role in obtaining α-Form crystals of Mirabegron in pure form.

α-Form crystals of Mirabegron of present invention is having good stability and purity in different conditions and can also be prepared by an efficient, economic and reproducible process particularly in large scale preparation with free flowing nature.

OBJECTIVE OF THE INVENTION

The main objective of the present invention is to provide a simple and cost effective process for the preparation of α-Form crystals of Mirabegron having good stability with high purity and good yield on a commercial scale.

SUMMARY OF THE INVENTION

In one aspect, the present invention provides a process for the preparation of α-Form crystals of Mirabegron comprising the steps of:
a) suspending Mirabegron in a solvent selected from water;
b) heating the suspension of step (a);
c) precipitating α-Form crystals of Mirabegron by cooling the suspension obtained in step (b);
d) isolating pure α-Form crystals of Mirabegron.

DETAILED DESCRIPTION OF THE INVENTION

Figure 1:
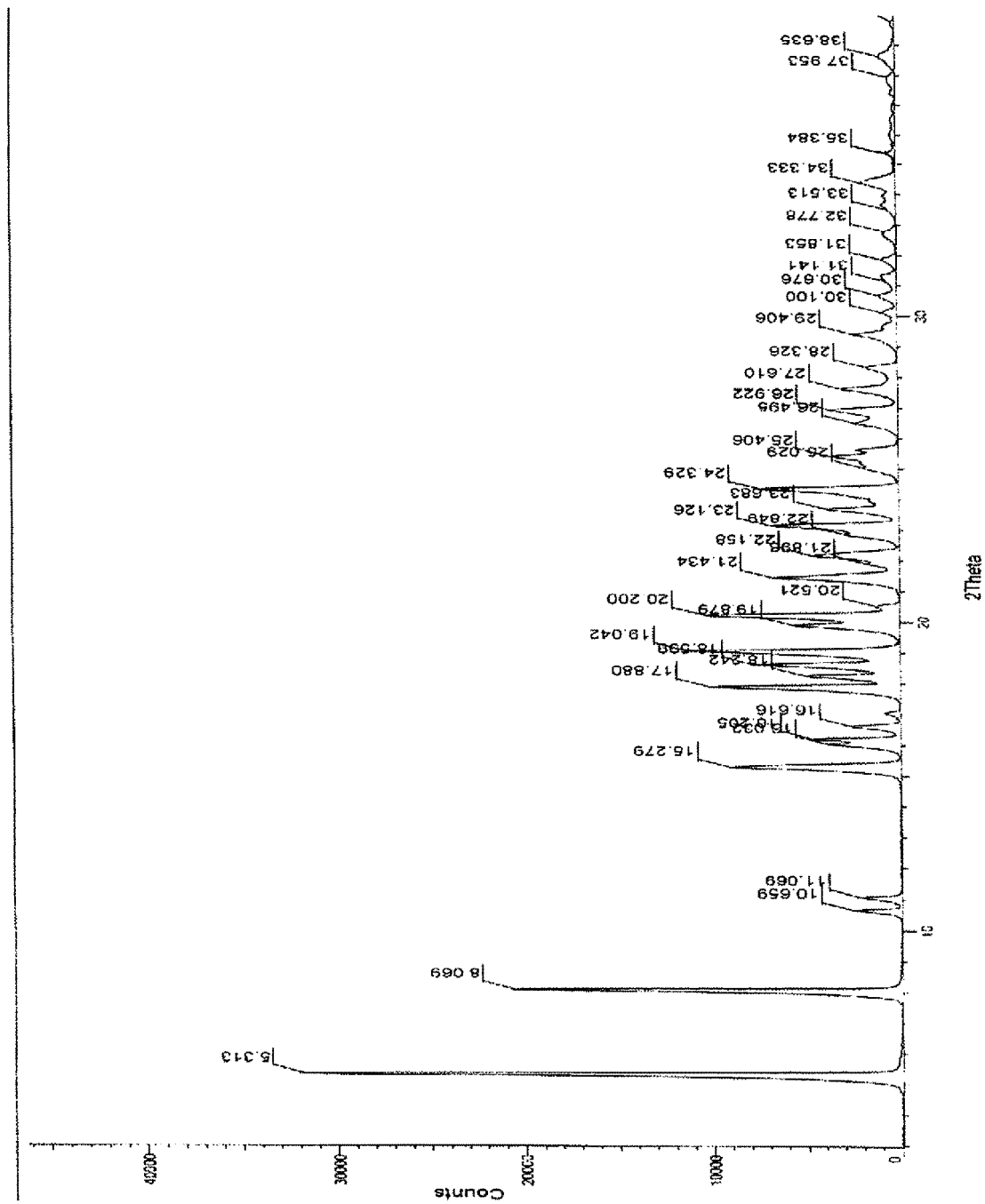
FIG. 1 Illustrates the X-ray powder diffraction pattern of α-Form crystals of Mirabegron produced by the present invention.
Figure 2:
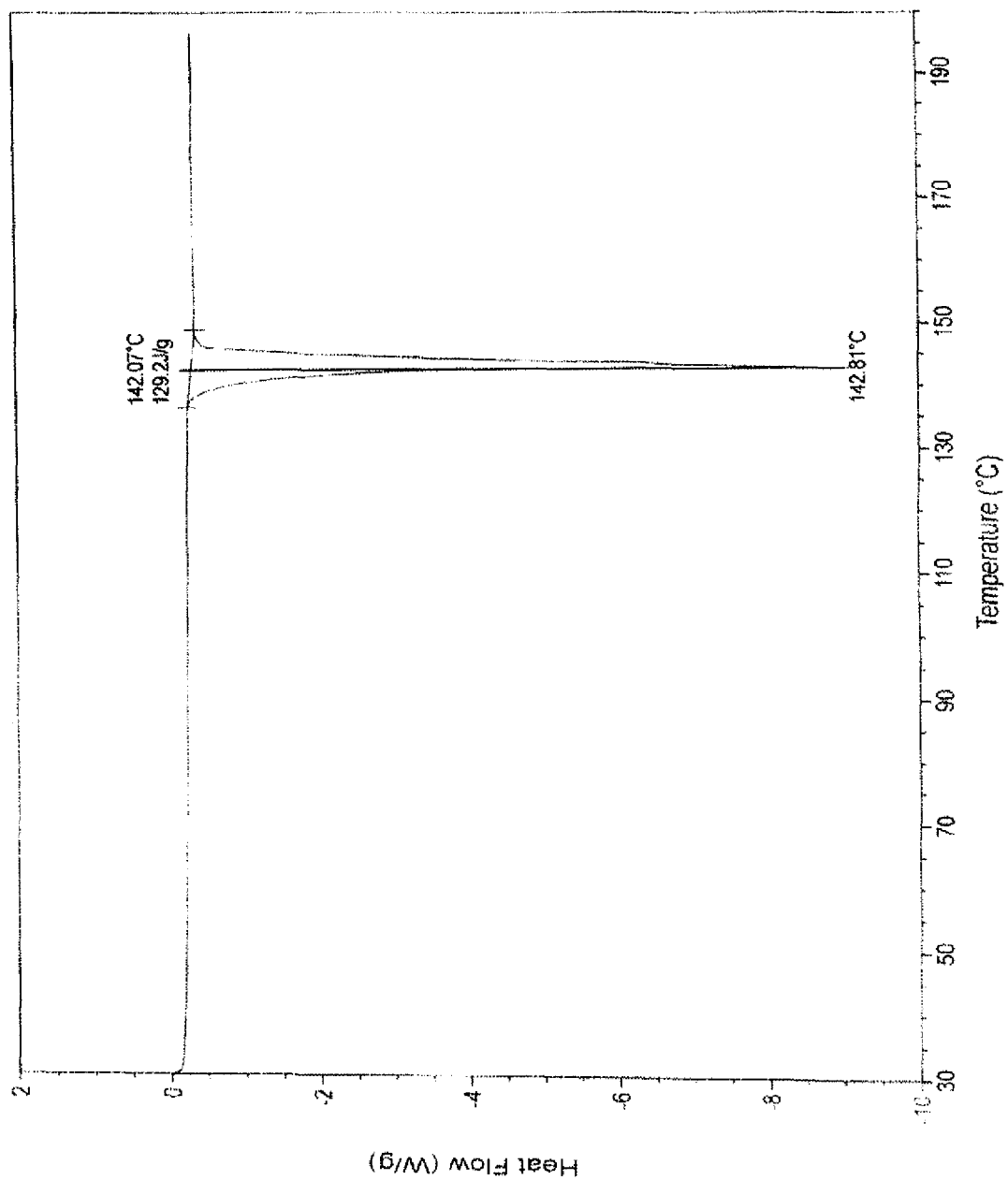
FIG. 2 Illustrates the differential scanning calorimetry of α-Form crystals of Mirabegron produced by the present invention.

In one aspect, the present invention provides a process for the preparation of α-Form crystals of Mirabegron comprising the steps of:

a) suspending Mirabegron in a solvent selected from water;
b) heating the suspension of step (a);
c) precipitating α-Form crystals of Mirabegron by cooling the suspension obtained in step (b);
d) isolating pure α-Form crystals of Mirabegron.

In another aspect, the Mirabegron is suspended in a solvent selected from water at a temperature about 10° C. to 35° C. The resulting suspension is heated at a temperature of about 50° C. to 90° C., continue stirring and monitor the complete conversion to α-Form crystals of Mirabegron by DSC. Thereafter, the suspension is cooled to 20-35° C. and slurry is stirred at same temperature for 1 to 5 hours.

In another aspect, the resulting slurry is optionally seeded with α-Form crystals of Mirabegron to obtained pure form of α-Form crystals of Mirabegron. The obtained α-Form crystals of Mirabegron are filtered and washed with water and finally dried at temperature about 45-75° C. under reducing pressure till the water content is ≤0.5% w/w.

In another aspect, Mirabegron used in present invention is prepared by condensing 4-nitrophenyl ethylamine hydrochloride (IV) with (R)-styrene oxide in the presence of a base in a solvent to produce (R)-1-phenyl-2-[[2-(4-nitrophenyl)ethyl]amino]ethanol (V), which is further protected with a protecting agent selected from tert-butoxy carbony group (Boc) in a solvent to produce tert-butyl-(R)-N-(2-hydroxy-2-phenylethyl)-N-[2-(4-nitro-phenyl)ethyl]carbamate (VI), which undergoes reduction in the presence of palladium-carbon and hydrogen in a solvent to produce tert-butyl-(R)-N-[2-(4-aminophenyl)-N-(2-hydroxy-2-phenylethyl)ethyl]-carbamate (VII). This compound (VII) is condensed with 2-amino-4-thiazoleacetic acid (III) in the presence of a base in a solvent to produce Boc-protected Mirabegron (VIII) and then treating with hydrochloride to produce Mirabegron dihydrochloride.

The process is as shown in Scheme-II below:

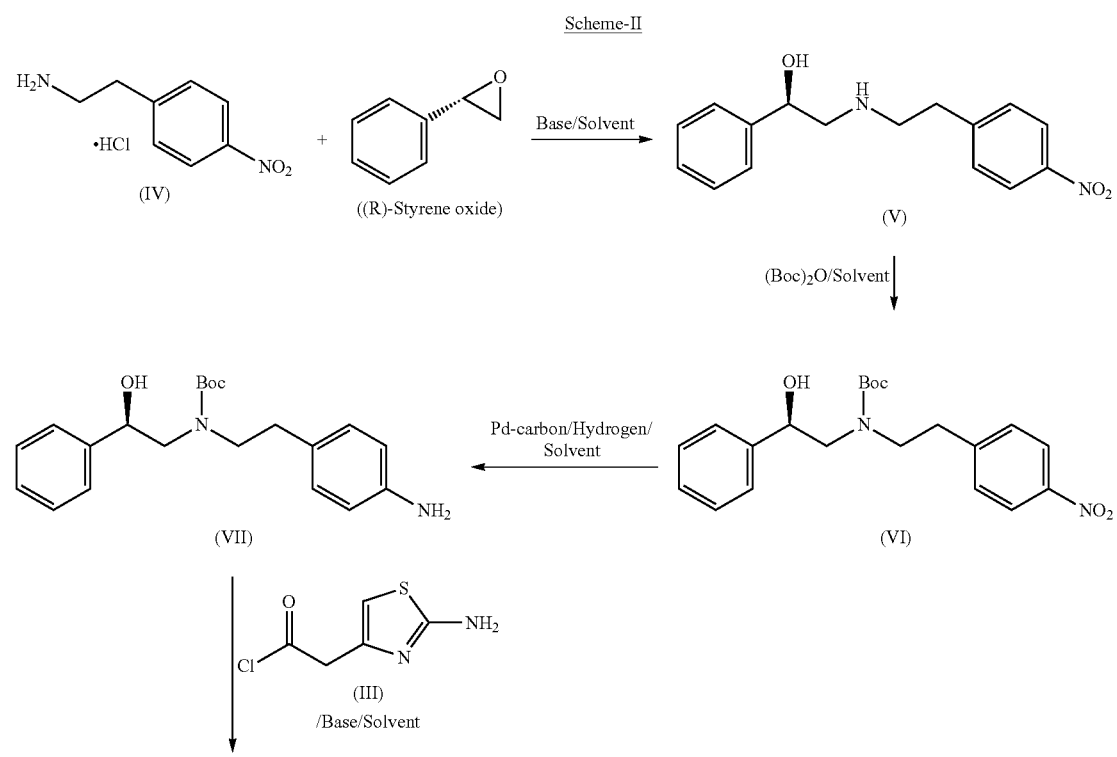

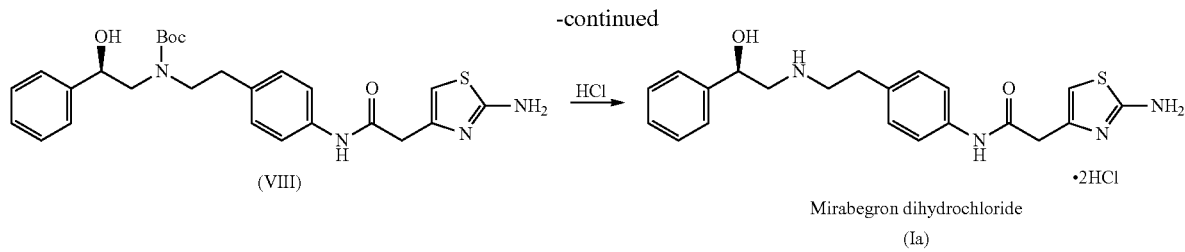

Mirabegron dihydrochloride
(Ia)

In another aspect, Mirabegron used in present invention is prepared by condensing compound of formula (IIa) with a compound of formula (IIIa) in a solvent followed by removal of protecting group to produce Mirabegron (I).

The process is as shown in Scheme-III below:

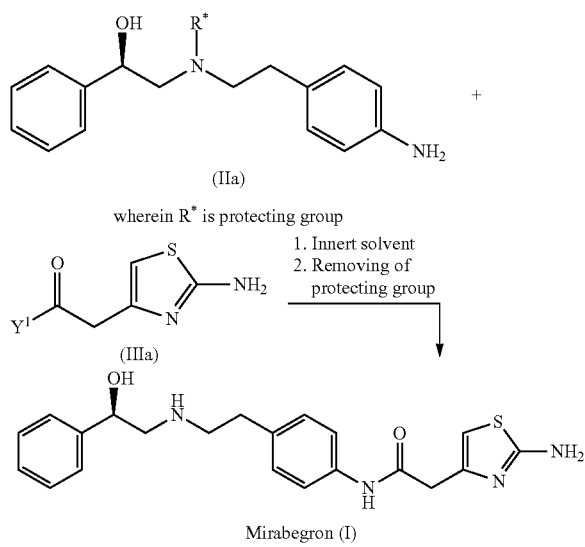

The following examples are provided to illustrate the invention and are merely for illustrative purpose only and should not be construed to limit the scope of the invention.

EXAMPLES

Preparation of α-Form Crystals of Mirabegron:

Example-1

Mirabegron (100 g) was suspended in DM water (1.50 Lt) at 25-30° C. The above suspension was cooled to 2-5° C. and concentrated hydrochloric acid (57.86 g, ~35% w/w Assay) was added at 2-5° C. slowly over a period of ~30 min. The suspension was stirred at 2-5° C. for ~30 min to obtain a clear solution and carbon enoanticromos (10 g) was added at 2-5° C. The stirring was continued at 2-5° C. for 30±10 min. Thereafter, carbon was removed by filtration through hyflo at 2-5° C. and the residue was washed with DM water (2×50 ml) at 2-5° C. In the meantime, sodium hydroxide (Reagent grade, 23.23 g) dissolved in DM water (500 ml), was added to the above filtrate at 2-5° C. slowly over a period of ~45 min during which Mirabegron precipitated out. The above contents were stirred at 2-5° C. for 1 h±10 min for complete precipitation of Mirabegron. Thereafter, the temperature of the above contents was raised to 20-25° C. The product was filtered and it washed with DM water (300 ml) at 20-25° C. The wet filtered mass was suspended in DM water (1.50 Lt) at 20-25° C. The suspension was heated to 70-75° C. The heating was continued at 70-75° C. and the complete conversion of Mirabegron α-Form crystals was monitored by DSC. Thereafter, the above suspension was cooled to 25-30° C. The slurry was stirred at 25-30° C. for 2 h±10 min. The product was filtered and washed it with DM water (100 ml×2) at 25-30° C. Finally, the product was dried at 50-60° C. under reduced pressure (20 mm Hg) till the water content is ≤0.3% w/w. Yield: Mirabegron α-Form crystals: 90 g.

Example-2

Mirabegron (30 g) was suspended in DM water (450 ml) at 25-30° C. The above suspension was cooled to 2-5° C. and concentrated hydrochloric acid (17.38 g, ~35% w/w assay) was added at 2-5° C. slowly over a period of ~30 min. The suspension was stirred at 2-5° C. for ~30 min to obtain a clear solution and carbon enoanticromos (3 g) was added at 2-5° C. The stirring was continued at 2-5° C. for 30±10 min. Thereafter, carbon was removed by filtration through hyflo at 2-5° C. and the residue was washed with DM water (30 ml) at 2-5° C. In the meantime, sodium hydroxide (Reagent grade, 6.97 g) dissolved in DM water (150 ml), was added to the above filtrate at 2-5° C. slowly over a period of ~45 min during which Mirabegron precipitated out. The above contents were stirred at 2-5° C. for 1 h±10 min for complete precipitation of Mirabegron. Thereafter, the temperature of the above contents was raised to 20-25° C. The product was filtered and it washed with DM water (3×30 ml) at 20-25° C. The wet filtered mass was suspended in DM water (450 ml) at 20-25° C. The suspension was heated to 70-75° C. The heating was continued at 70-75° C. and the complete conversion of Mirabegron α-Form crystals was monitored by DSC. Thereafter, the above suspension was cooled to 25-30° C. The slurry was stirred at 25-30° C. for 2 h±10 min. The product was filtered and washed it with DM water (30 ml×2) at 25-30° C. Finally, the product was dried at 50-60° C. under reduced pressure (20 mm Hg) till the water content is ≤0.3% w/w. Yield: Mirabegron α-Form crystals: 21.86 g.

We claim:

1. A process for the preparation of α-Form crystals of Mirabegron comprising the steps of:
    (a) suspending Mirabegron in water;
    (b) heating the suspension of step (a);
    (c) precipitating α-Form crystals of Mirabegron by cooling the suspension obtained in step (b);
    (d) isolating pure α-Form crystals of Mirabegron.

2. The process as claimed in claim 1, the resulting suspension in step-(b) is optionally seeded with α-Form crystals of Mirabegron to obtain pure form of α-Form crystals of Mirabegron.

3. The process as claimed in claim 1, the α-Form crystals of Mirabegron have water content≤0.5% w/w.

4. The process as claimed in claim 1, suspending Mirabegron in water at a temperature about 10° C. to 35° C.

5. The process as claimed in claim 1, heating the suspension at a temperature of about 50° C. to 90° C.

\* \* \* \* \*